United States Patent [19]

Staub et al.

[11] Patent Number: 5,162,331
[45] Date of Patent: Nov. 10, 1992

[54] ASPERNOMINE, AN ANTIINSECTAN METABOLITE

[75] Inventors: Gail M. Staub, Iowa City, Iowa; Patrick F. Dowd, Peoria, Ill.; James B. Gloer, Iowa City, Iowa; Donald T. Wicklow, Peoria, Ill.

[73] Assignees: The United States of America as represented by the Secretary of Agriculture, Washington, D.C.; University of Iowa Research Foundation, Iowa City, Iowa; Biotechnology Research & Development Corporation, Peoria, Ill.

[21] Appl. No.: 732,604

[22] Filed: Jul. 19, 1991

[51] Int. Cl.$^5$ .......................................... C07D 221/22
[52] U.S. Cl. ...................................... 514/281; 546/43
[58] Field of Search ............................ 514/281; 546/43

[56] References Cited

U.S. PATENT DOCUMENTS 5,017,598  5/1991  Dowd et al. ..................... 514/415

OTHER PUBLICATIONS

Gloer et al. "Nominine: A New Insecticidal Indole Diterpene from the Sclerotia of *Aspergillus nomius*". J. Org. Chem, vol. 54, 1989, pp. 2530–2532.

Kurztman et al. "*Aspergillus nomius*, A New Aflatoxin-- Producing Species Related to *Aspergillus flavus* and *Aspergillus tamarii*.", Antonie Van Leeuwenhoek, vol. 53, 1987, pp. 147–158.

*Primary Examiner*—Donald G. Daus
*Attorney, Agent, or Firm*—Arnold, White & Durkee

[57] ABSTRACT

A tetrahydroquinoline alkaloid compound named "aspernomine" has been isolated from the sclerotia of the fungus *Aspergillus nomius*. Aspernomine has the structure:

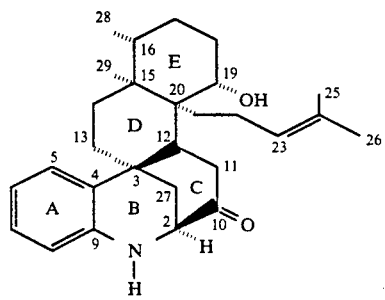

and is effective for controlling Lepidopteran insects.

7 Claims, No Drawings

ASPERNOMINE, AN ANTIINSECTAN METABOLITE

BACKGROUND OF THE INVENTION

1. Field of the Invention

The present invention is generally related to tetrahydroquinoline alkaloid compounds. More specifically, the tetrahydroquinoline alkaloid compound is used as an insecticide for control of Lepidoptera species.

2. Background of the Art

Certain fungi produce specialized resting bodies known as sclerotia as a means for surviving adverse environmental conditions which other fungal bodies cannot tolerate, such as harsh climate, nutrient deficiency and desiccation. Generally, sclerotia remain viable in soil for periods of several years, and provide primary inoculum for the producing species when conditions again become favorable for fungal growth. Sclerotia are formed under natural conditions or in solid substrate fermentations, but are not commonly produced in the liquid fermentation cultures generally employed in studies of microbial metabolites. Accordingly, many novel sclerotial metabolites of common fungi such as Aspergillus have not been characterized.

While sclerotia are known to contain biologically active secondary metabolites not found in other fungal parts or in liquid cultures, study of sclerotia as sources of novel metabolites has been limited. Investigation of large sclerotia (ergots) of *Claviceps purpurea* led to the discovery and medicinal use of ergot alkaloids.

Sclerotia have recently been recognized as a valuable potential source for natural antiinsectans. Many sclerotia, which are subjected to predation by fungivorous insects and anthropods during their period of dormancy in soil, have been shown to contain metabolites that exert adverse physiological effects on insects. Gloer et al. [*J. Org. Chem.* 53: 5457 (1988)] and Wicklow et al. [*Trans. Br. Mycol. Soc.* 91: 433 (1988)] disclose the isolation of four antiinsectan aflavanine derivatives from the sclerotia of *Aspergillus flavus* for use in controlling the dried-fruit beetle *Carpophilus hemipterus* (Nitidulidae:-Coleoptera). TePaske et al. [*J. Org. Chem.* 55: 5299 (1990)] disclose a related metabolite, aflavazole, which was isolated from extracts of *A. flavus* sclerotia. Gloer et al. [*J. Org. Chem.* 54: 2530 (1989)] describe an insecticidal indole diterpene known as nominine found only in the sclerotia of *Aspergillus nomius* for the control of the corn earworm *Helicoperva zea* (Lepidoptera), formerly *Heliothis zea*. Nominine is also disclosed by Dowd et al. in U.S. Pat. No. 5,017,598 issued May 21, 1991, and entitled "Nominine, an Insecticidal Fungal Metabolite".

There remains a continuing need for new insecticides because many agriculturally important insect species have developed a resistance to the most potent insecticides which are currently available. Moreover, environmentally tolerable replacements for these insecticides are declining. New natural, biodegradable insecticides which are relatively nontoxic to vertebrates and may be produced by fermentation processes are a cost effective replacement for known insecticides.

SUMMARY OF THE INVENTION

In order to satisfy the need for a cost effective, natural, biodegradable insecticide, one aspect of the present invention provides a substantially pure tetrahydroquinoline alkaloid compound. This "aspernomine" compound is isolated from the sclerotia of the fungus *Aspergillus nomius* and is effective for controlling Lepidopteran insects. The compound has the structure:

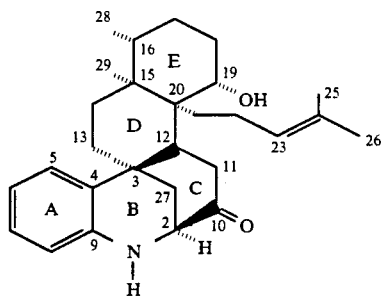

Another aspect of the present invention provides a composition for controlling insects containing the aspernomine compound and an inert carrier. The aspernomine compound is preferably present in the composition in an amount effecting insects of the Lepidopteran species, such as *Helicoverpa zea*. An effective amount of the composition may be applied to a locus of insects in order to control the insects.

DETAILED DESCRIPTION OF THE INVENTION

The present invention provides a substantially pure tetrahydroquinoline alkaloid compound effective in controlling insects, insecticidal compositions containing the compound of the present invention and a method for controlling insects by applying the compositions to the locus of the insects.

The tetrahydroquinoline alkaloid compound of the present invention has been designated "aspernomine". The aspernomine compound, which is effective for controlling Lepidopteran insects, has the structure:

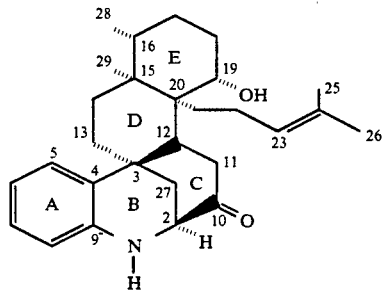

The aspernomine compound is isolated from the sclerotia of the fungus *Aspergillus nomius*, a member of the *A. flavus* taxonomic group. A strain of the fungus *Aspergillus nomius* was deposited on Jun. 10, 1991 in the Agricultural Research Service Patent Culture Collection (NRRL) in Peoria, Ill. and has been assigned Deposit No. NRRL 18836. The culture deposit will be stored and made available to the public in accord with the provisions of the Budapest Treaty for the Deposit of Microorganisms. All restrictions on the availability of the culture deposit to the public will be irrevocably removed upon the granting of a patent disclosing the strain.

The sclerotia of *A. nomius* are produced by solid-substrate fermentation on corn kernels. They are ground by conventional means to a suitable particle size and are extracted with at least one solvent. Suitable solvents for the extraction could be readily determined by the skilled artisan and would include any solvents in which the aspernomine compounds of the present invention are soluble. Preferably, the ground sclerotia are extracted with pentane and are subsequently extracted with a hexaneethyl acetate gradient.

Isolation and purification of the aspernomine compound from the solvent extract is effected by the use of conventional techniques, such as high-performance liquid chromatography (HPLC), thin layer chromatography (TLC), silica gel column chromatography and countercurrent distribution (CCD). In the preferred embodiment of the invention, the pentane extract is concentrated to afford a yellow-orange oil. The oil was subjected to silica gel column chromatography. Aspernomine was obtained as white needles upon evaporation of selected fractions eluted with hexane. The details of the isolation procedure are described in Example 1, although the procedure is not limited thereto.

Commercial formulations including the aspernomine compound may be prepared directly from fungal extracts or from the fractions derived from the extracts. However, the formulations are prepared from a pure or a substantially pure aspernomine when a high degree of specificity is required. For example, if a high degree of predictability of the intended response by both target and nontarget species is required, a formulation prepared from a pure or substantially pure form of an aspernomine would be used. The formulation would then exclude other substances found in natural fungi which might have an adverse effect on activity or a toxic effect toward nontarget species.

Insecticidal compositions of the present invention include the aspernomine as described above in combination with a suitable inert carrier as known in the art. Agronomically acceptable carriers such as alcohols, ketones, esters and surfactants are illustrative. Aspernomine is present in the composition in an amount effecting the target species which is typically at least about 1.0 ppm. The concentration of the aspernomine compound in an insecticidal composition will vary considerably depending upon the target species, substrate, method of application and desired response. Additional factors to be considered in determining an optimum concentration include phytotoxicity toward the treated plant and the tolerance of nontarget species.

The aspernomine compound acts to control pests by mechanisms including growth regulation, death inducement, sterilization, as well as interference with metamorphosis and other morphogenic functions. The resulting response is dependant on the pest species, aspernomine concentration and method of application. The aspernomine compound is administered in an amount effecting one or more of the responses as may be predetermined by routine testing. Where the intended response is pest mortality, an "effective amount" is defined as the quantity of aspernomine compound which will effect a significant mortality rate of a test group as compared with an untreated group. The actual effective amount will vary with the species of pest, stage of larval development, nature of the substrate, the type of inert carrier, the period of treatment and other related factors.

The compositions of the present invention are effective in controlling a variety of insects. Agronomically important insects such as those of the orders Lepidoptera and Coleoptera are of particular interest. However, the compounds and compositions of the present invention are not limited thereto.

The insecticidal compositions of the present invention are used to control insects by applying the composition to the locus of the pest to be controlled. When the aspernomine compound is intended as a stomach poison, it is applied in conjunction with an inert carrier to the pest diet. The composition is applied to plants by treating the leaf surfaces or by systematic incorporation. As a contact poison, any topical method of application will be effective, such as direct spraying on the pest or on a substrate which is likely to be contacted by the pest.

The following examples are presented to describe preferred embodiments and utilities of the present invention and are not meant to limit the present invention unless otherwise stated in the claims appended hereto.

EXAMPLE 1

Isolation and Purification of Aspernomine

A strain of *A. nomius* (NRRL 18836) originally isolated from a pine sawfly (*Diprion similis*) was obtained from the ARS Culture Collection at the USDA Northern Regional Research Center in Peoria, Ill. Sclerotia were prepared by solid substrate fermentation of *A. nomius* on autoclaved corn kernels using procedures described by Wicklow et al. in supra (1988), and were stored at 4° C. until extraction. Sclerotia of *A. nomius* (120.8 g) were ground with a mortar and pestle and then extracted with n-pentane in a soxhlet apparatus for 54 hours. Concentration of the resulting N-pentane extract afforded 297 mg of a yellow-orange oil. A portion of this extract (80 mg) was subjected to silica gel chromatography (26×1.5 cm column) using a hexane-ethyl acetate gradient, collecting 4-ml fractions. Aspernomine was obtained as white needles (6.7 mg) upon evaporation of selected fractions eluted with 90% hexane. This procedure was repeated with the remaining extract to yield a total of 18.8 mg of aspernomine.

In determining the properties of aspernomine, carbon multiplicites were determined by a distortionless enhancement by polarization transfer (DEPT) experiment. One-bond C-H correlations were obtained using a heteronuclear multiple quantum correlation (HMQC) experiment optimized for 120 Hz. Proton assignments were made by analysis of correlated spectroscopy (COSY), homonuclear decoupling, and HMQC experiments. Axial and equatorial orientations were determined where possible on the basis of coupling constants and nuclear overhauser enhancement/exchange spectroscopy (NOESY) interactions. Long-range C-H correlations were obtained either by selective insensitive nuclei enhanced by polarization transfer (INEPT) experiments or by a heteronuclear multiple bond correlation (HMBC) experiment optimized for 8.5 Hz. All 2D-NMR experiments were conducted at 600 MHz. Individual proton signals studied using the selective INEPT technique were subjected to as many as five separate experiments optimizing for 5, 7, 8, 10 or 12 Hz.

Aspernomine has the following characteristics: $[\alpha]_D+225°$ (c=0.12 g/dl; MeOH, 27° C.); $^1$H NMR, $^{13}$C NMR, NOESY, and HMBC data in Table 1; UV (MeOH) 336 ($\epsilon$1150), 302 (2510), 244 (5760), 232 (5460); IR (neat) 3500, 3360, 2970, 2930, 1698, 1606, 1490, 750 cm$^{-1}$; Electron impact mass spectrometry (EIMS) (70 eV) 421 (M$^+$; rel. int. 4%), 184 (7), 156 (100), 143 (37), 130 (28); High resolution electron impact mass spectrometry (HREIMS) obsd. 421.3024, calcd. for $C_{28}H_{39}NO_2$, 421.2981.

TABLE 1

Proton and Carbon-13 NMR Data[a] for Aspernomine in $CDCl_3$

| Position | $^1H$ | $^{13}C$ | HMBC/Sel. INEPT | NOESY |
|---|---|---|---|---|
| 1 | 4.35(br s) | | | 2,8 |
| 2 | 3.75(br s) | 56.97(d) | 3[b],9[b],10[b] | 1[c],22a,25,21b,27b[c] |
| 3 | | 36.30(s) | | |
| 4 | | 130.70(s) | | |
| 5 | 7.43(brd; 8.7) | 125.59(d) | 3,7,9 | 13ax |
| 6 | 6.77(dd; 8.7,7.9) | 118.37(d) | 4,8 | |
| 7 | 7.04(dd; 8.7) | 127.58(d) | 5,9 | |
| 8 | 6.51(brd; 8.7) | 114.65(d) | 4,6 | 1 |
| 9 | | 142.70(s) | | |
| 10 | | 209.20(s) | | |
| 11a | 2.11(dd; 6.2,17.6) | 37.33(t) | 10,12[e],20[e] | 12[c],19 |
| 11b | 2.47(d; 17.6) | | 2,3,10,20[e] | 12[c],19,22a,25 |
| 12 | 2.64(br d; 8.3) | 47.25(d) | 3,4,10,11,19,20,21[e],27 | 11a[c],11b[c],16,19 |
| 13eq | 1.27(m) | 30.62(t) | | |
| 13ax | 2.58(ddd; 4.1,14.5,14.5) | | 3,4,14,27 | 5,14eq[c] |
| 14eq | 1.39(m) | 28.95(t) | | |
| 14ax | 1.68(m) | | | |
| 15 | | 40.09(s) | | |
| 16 | 2.40(m) | 31.33(d) | 15,28 | 12 |
| 17a | 1.36(m) | 24.97(t) | | |
| 17b | 1.72(m) | | | |
| 18eq | 1.57(m) | 29.92(t) | | |
| 18ax | 1.82(m) | | | |
| 19 | 4.01(br s) | 69.84(d) | 15,17 | 11a,11b,12,18eq[c],22b |
| 20 | | 46.38(s) | | |
| 21a | 1.30(m) | 30.20(t) | | |
| 21b | 1.64(m) | | | |
| 22a | 1.98(br d; 10.3) | 23.88(t) | 20[e],21[c],23,24 | 2,11b,23[c],25,29 |
| 22b | 2.20(m) | | 20,23,24 | 19,23[c],25 |
| 23 | 5.01(br t) | 125.59(d) | 21,25,26 | 25,26[d] |
| 24 | | 131.72(s) | | |
| 25 | 1.60(s) | 17.91(q) | 23,24,26 | 2,22a,22b,23,28,29 |
| 26 | 1.67(s) | 25.57(q) | 23,24,25 | 23,28 |
| 27a | 1.79(br d; 13.4) | 34.63(t) | 2,3,10,12 | |
| 27b | 2.93(br dd; 2.1,14.5) | | 3,4 | |
| 28 | 0.93(d; 7.7) | 15.92(q) | 15,16,17 | 14eq,16[c],25,26,29 |
| 29 | 1.09(s) | 18.84(q) | 14,15,16,20 | 14eq,22a,25,28 |

[a]Data were collected at 600 and 90.7 MHz, respectively.
[b]These signals were observed in selective INEPT experiments, but not in the HMBC experiment.
[c]These correlations involve proton signals that are also scalar coupled.
[d]The NOESY interaction for this signal with $H_3$-26 was much more intense than that observed for $H_3$-25.
[e]These correlations were observed in the HMBC experiment, but selective INEPT results were obtained to confirm the precise locations of the corresponding carbon signals. A number of overlapping proton signals gave HMBC or NOESY cross-peaks that could not be unambiguously assigned, but none of these correlations were inconsistent with the proposed structure.

The molecular formula $C_{28}H_{39}NO_2$, as determined by $^{13}C$ NMR and HREIMS data, differed from that of nominine by the addition of one oxygen atom. NMR data indicated some similarities between the two compounds. However, the appearance of the NH proton chemical shift at 4.35 ppm as compared to 7.88 ppm for nominine, along with other differences in the UV and $^{13}C$ NMR spectra, indicated the absence of an indole moiety. In addition, $^{13}C$ NMR and IR data revealed the presence of a ketone functionality (209.2 ppm and 1698 $cm^{-1}$, respectively). Thus, it was clear that the structure of aspernomine is significantly different from that of nominine. Proton spin systems were determined by analysis of a series of decoupling experiments and a homonuclear proton COSY spectrum recorded at 600 MHz. Shift assignments for carbons bound to hydrogen atoms were established on the basis of an HMQC experiment as described by Bax and Subramanian in *J. Magn. Reson.* 67:565 (1986). The remaining carbon NMR assignments and the connectivity of the spin systems were determined with the aid of long-range C—H correlations obtained through HMBC and selective INEPT experiments as disclosed by Bax and Summers in *J. Am. Chem. Soc.* 108:2093 (1986) and Bax, *J. Mag. Reson.* 57:314 (1984), respectively.

The presence of a 1,2-disubstituted benzene ring, and isolated $NHCHCH_2$, $CHCH_2$, and 4-methyl-3-pentenyl units were established from the COSY, decoupling, and HMQC data. The following partial structure

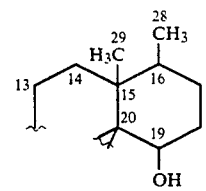

a structural subunit found in nominine, was also initially proposed by comparison of NMR data with those obtained for nominine. HMBC correlation of $H_3$-28 with C-15, 16 and 17, and correlation of $H_3$-29 with C-14, 15, 16 and 20, along with other supporting data, confirmed the partial structure. These five spin systems accounted for all of the carbons except for the ketone carbon and one additional aliphatic quaternary carbon. Connectivity of these units was elucidated by analysis of longrange C—H correlations. The attachment of the 4-methyl-3-pentenyl group to C-20 was established by a correlation of one of the C-22 protons (2.20 ppm) with this carbon. Correlation of the methine proton of the NHCHCH$_2$ unit (H-2) with C-9 of the 1,2-disubstituted aromatic ring, in conjunction with the downfield chemical shift of C-9 (142.7 ppm), linked the aromatic ring with the nitrogen atom of the NHCHCH$_2$ unit. An HMBC cross-peak between the signal for the aromatic proton H-5 and the additional aliphatic quaternary carbon resonance (C-3) placed C-3 on the aromatic ring ortho to the nitrogen atom. The methine proton H-12 of the isolated CHCH$_2$ unit (comprised of C-12 and C-13) showed a variety of HMBC cross-peaks that were especially useful in determining the structure of aspernomine. Correlations of the H-12 proton signal to both C-3 and C-4 indicated that C-12 is connected to C-3. Correlations of H-12 to C-19 and C-20 of the structural subunit, as well as to C-21 of the 4-methyl-3-pentenyl sidechain, revealed the direct connection of C-12 to C-20. Thus, these results permitted assignment of all of the atoms directly linked to C-12. A further correlation of the H-12 proton to the methylene carbon of the isolated NHCHCH$_2$ unit (C-27) implied connection of C-27 to C-3 to form the six-membered B-ring, since C-27 cannot be directly attached to C-12, C-11 or the NH group. The remaining atom linked to the quaternary carbon C-3 was established as C-13 of the structural subunit based on observation of correlations of the downfield-shifted H$_{ax}$-13 proton with C-3, C-4 and C-27. These results also confirmed the linkage of C-27 to C-3.

A final correlation of H-12 with the ketone carbon (C-10) showed that C-10 must be connected either to C-11 or to C-3. Since all of the connections to C-3 are already connected for, C-10 must be attached to C-11. Supporting evidence was provided by additional correlations of C-10 with H-2, H$_a$-11, and H$_a$-27. The only remaining positions available for connection are C-10 and C-2. Linkage of these two positions is supported by HMBC correlations of C-2 with C-10, and of one of the C-11 protons with C-2. Based on these and other supporting data, the gross structure of aspernomine which has a previously unreported ring system was assigned.

The relative stereochemistry of the E-ring and the D/E ring fusion of aspernomine (positions 15, 16, 19 and 20) is proposed to be analogous to that of nominine and other related Aspergillus metabolites based on biogenetic and NMR similarities. Confirmation of this hypothesis was obtained through NOESY data as shown in Table 1. A NOESY correlation was observed between H-12 and H-16. In order for these two protons to be spatially close, the relative stereochemistry at positions 15, 16 and 20 must be as shown. Furthermore, both protons must be axial (H-12 axial with respect to the D-ring), with the D- and E-rings most likely adopting a chair-chair conformation. Nominine and the aflavinines possess a similar cis D/E-ring fusion. Additional supporting evidence was provided by NOESY correlations between H$_3$-28 and H$_3$-29, and between H$_3$-29 and one of the protons on C-22. H-19 must have an equatorial disposition (no trans-diaxial coupling with either neighboring proton). This observation, along with NOESY correlations of H-19 with both H-11 protons, plus a weak correlation with H-12, establishes the relative stereochemistry at C-19 as shown. The remaining relative stereochemical assignments were proposed on the basis of other NOESY correlations and on geometrical considerations. A strong correlation of the axial proton on C-13 with H-4 of the aromatic ring led to assignment of the sterochemistry indicated at position 3. This assignment would also rationalize the substantial downfield shift of H$_{ax}$-13 (2.58 ppm) due to aromatic ring current effects. Geometrical constraints of the bridged B/C-ring system require that H-2 must be cis to C-13 with respect to the B-ring. The NOESY correlations mentioned earlier between the C-11 protons and H-19, and between H-12 and H-16 require the relative configuration shown for the remaining stereocenter (C-12). The C-ring would have to adopt a twisted conformation rather than the alternative chairlike form in order to account for proximity of both C-11 protons to H-19.

It is likely that nominine and aspernomine compounds arise biogenetically from a common geranylgeranyl indole precursor. The pathway to aspernomine appears to involve unusual steps. The non-trivial skeletal differences between nominine and aspernomine suggest that nominine is not a precursor to aspernomine, and that the divergence may occur significantly earlier in the biosynthetic process.

EXAMPLE 2

Insecticidal Activity of Aspernomine

The compound was evaluated by insect bioassays described previously by Dowd in *Entomol. Exp. Appl.* 47:69 (1988). Neonate larvae of *H. zea* were used for all assays. They were obtained from laboratory colonies reared on pinto bean-based diet at 27° C.,±1° C., 40±10% relative humidity, and a 14:10 light:dark photoperiod.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. The aspernomine was added in 125 μl of acetone to the liquid diet to give a final concentration of 100 ppm. Upon addition of the aspernomine, the mixture was removed from the water bath. The chemical was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 min until slight darkening occured. The diets were cut into approximately equal sections, and each section was placed into a well of a 24-well immunoassay plate. A single neonate *H. zea* was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4 and 7 days, and the surviving larvae were weighed after 7 days. Each chemical set was tested on a total of 20 larvae.

Aspernomine, a tetrahydroquinoline alkaloid, exhibits significant activity against the corn earworm *H. zea*. Incorporating this compound into a standard test diet at 100 ppm (dry weight) caused a 35.4% reduction in weight gain of the test insects relative to controls. This compound also exhibits moderate cytotoxicity against three human solid tumor cell lines. $ED_{50}$ values of 3.09, 4.93 and 3.08 μg/ml were observed in assays against A-549 lung carcinoma, MCF-7 breast adenocarcinoma and HT-29 colon adenocarcinoma cell lines, respectively.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

We claim:

1. A substantially pure tetrahydroquinoline alkaloid designated aspernomine and having the structure:

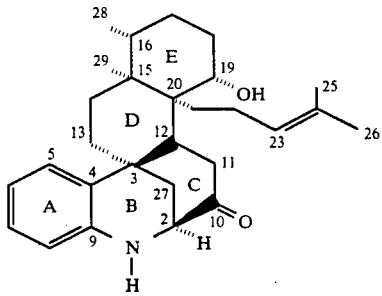

2. In insecticidal composition comprising substantially pure aspernomine and an agro nomically acceptable inert carrier.

3. The composition of claim 2 including an amount of aspernomine effecting insects of the Lepidoptera species.

4. The composition of claim 2 including an amount of aspernomine effecting *Helicoverpa zea*.

5. A method of controlling insects comprising applying an effective amount of substantially pure aspernomine to a locus of insects.

6. The method of claim 5 wherein the insects are Lepidoptera species.

7. The method of claim 5 wherein the insects are *Helicoverpa zea*.

* * * * *